(12) United States Patent
Bahr et al.

(10) Patent No.: US 6,647,280 B2
(45) Date of Patent: *Nov. 11, 2003

(54) METHOD AND APPARATUS FOR PROCESSING A PHYSIOLOGICAL SIGNAL

(75) Inventors: Dennis E. Bahr, Madison, WI (US); James L. Reuss., Waukesha, WI (US)

(73) Assignee: OB Scientific, Inc., Germantown, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/047,356

(22) Filed: Jan. 14, 2002

(65) Prior Publication Data

US 2002/0099281 A1 Jul. 25, 2002

Related U.S. Application Data

(63) Continuation of application No. 09/410,887, filed on Sep. 30, 1999, now Pat. No. 6,339,715.

(51) Int. Cl.[7] .................................................. A61B 5/00
(52) U.S. Cl. ........................ 600/323; 702/75; 702/76; 704/214; 704/208; 704/267; 600/309; 600/310; 600/336
(58) Field of Search ...................... 702/75–76; 704/214, 704/208, 207; 600/309–310, 336, 323, 330, 473, 476

(56) References Cited

U.S. PATENT DOCUMENTS

| 4,770,184 A | 9/1988 | Greene, Jr. et al. |
| 4,776,339 A | 10/1988 | Schreiber et al. |
| 4,894,795 A | 1/1990 | Whitehouse et al. |
| 4,928,692 A | 5/1990 | Goodman et al. |
| 4,947,857 A | 8/1990 | Albert et al. |
| 5,109,846 A | 5/1992 | Goodman et al. |
| 5,233,991 A | 8/1993 | Wright |
| 5,425,362 A | 6/1995 | Siker et al. |
| 5,430,690 A | 7/1995 | Abel |
| RE35,122 E | 12/1995 | Coreman et al. |
| 5,490,505 A | 2/1996 | Diab et al. |
| 5,494,032 A | 2/1996 | Robinson et al. |
| 5,497,771 A | 3/1996 | Rosenheimer |
| 5,564,428 A | 10/1996 | Soermo et al. |
| 5,588,425 A | 12/1996 | Sackner et al. |
| 5,594,655 A | 1/1997 | Berchin |
| 5,620,002 A | 4/1997 | Hughes |
| 5,632,272 A | 5/1997 | Diab et al. |

(List continued on next page.)

FOREIGN PATENT DOCUMENTS

WO    WO 01/24042 A1    4/2001

OTHER PUBLICATIONS

Springer, Tom: "Sliding FFT computes frequency Spectra in real time" Sep. 29, 1998 EDN, p. 161–170.
Tom Springer, Sep. 29, 1988, pp. 161–170, Sliding FFT Computes Frequency Spectra in Real Time.
Rusch et al.: "Signal Processing Methods for Pulse Oximetry" Mar. 1, 1996, Computers in Biology and Medicine, p. 143–159.

*Primary Examiner*—Eric F. Winakur
*Assistant Examiner*—Matthew J Kremer
(74) *Attorney, Agent, or Firm*—Peinhart Boerner Van Deuren s.c.

(57) ABSTRACT

A signal processing method, preferably for extracting a fundamental period from a noisy, low-frequency signal, is disclosed. The signal processing method generally comprises calculating a numerical transform for a number of selected periods by multiplying signal data by discrete points of a sine and a cosine wave of varying period and summing the results. The period of the sine and cosine waves are preferably selected to have a period substantially equivalent to the period of interest when performing the transform.

10 Claims, 4 Drawing Sheets

U.S. PATENT DOCUMENTS

| | | |
|---|---|---|
| 5,680,868 A | 10/1997 | Kahn et al. |
| 5,687,722 A | 11/1997 | Tien et al. |
| 5,772,600 A | 6/1998 | Kahn et al. |
| 5,776,058 A | 7/1998 | Levinson et al. |
| 5,778,337 A | 7/1998 | Ireton |
| 5,813,980 A | 9/1998 | Levinson et al. |
| 5,823,952 A | 10/1998 | Levinson et al. |
| 5,842,981 A | 12/1998 | Larsen et al. |
| 5,853,364 A | 12/1998 | Baker, Jr. et al. |
| 5,857,462 A | 1/1999 | Thomas et al. |
| 5,873,836 A | 2/1999 | Kahn et al. |
| 5,911,690 A | 6/1999 | Rall |
| 5,917,919 A | 6/1999 | Rosenthal |
| 5,919,134 A | 7/1999 | Diab |
| 5,924,979 A | 7/1999 | Swedlow et al. |
| 5,934,277 A | 8/1999 | Mortz |
| 5,960,373 A | 9/1999 | Fukuda et al. |
| 6,005,658 A | 12/1999 | Kaluza et al. |
| 6,014,617 A | 1/2000 | Kawahara |
| 6,083,172 A | 7/2000 | Baker et al. |
| 6,094,592 A | 7/2000 | Yorkey et al. |
| 6,339,715 B1 * | 1/2002 | Bahr et al. .................. 600/323 |

* cited by examiner

METHOD AND APPARATUS FOR PROCESSING A PHYSIOLOGICAL SIGNAL

CROSS REFERENCE TO RELATED APPLICATIONS

This application is a continuation of application Ser. No. 09/410,887, filed on Sep. 30, 1999 now U.S. Pat. No. 6,339,715.

FIELD OF THE INVENTION

The present invention relates to the field of signal processing. More specifically, the present invention relates to a numerical transform for obtaining a fundamental period from a signal, particularly for a numerical transform method suitable for determining the period and filtering noise from a physiological signal. The present invention is particularly suitable for use in oximetery applications.

BACKGROUND

In medical or physiological monitoring, physiological measurements required to determine parameters such as blood pressure and blood oxygen saturation levels are often dependent on a valid comparison of monitored waveforms or data to the patient's heart pulse.

For example, commercially available pulse oximeters generally measure energy attenuation or light absorption in biological tissue to determine blood oxygen saturation levels. One common type of pulse oximeter employs light in two wavelengths to obtain the arterial oxygenation level, wherein light in the red range and light in the infrared range are directed at the patient and detected by a photodetector. With each cardiac cycle, there is cyclic light absorption by tissue beds. During diastole, absorption is a result of venous blood, tissue, bone and pigments. During systole, light absorption is increased by the influx of arterialized blood into the tissue bed. The resulting pulsatile variation absorption through time is called the plethysmographic signal.

The oximeter determines the difference between background absorption during diastole and peak absorption during systole at both red and infrared wavelengths, as this difference corresponds to the absorption caused by arterialized blood. Since oxygen saturation determines the red:infrared light absorption ratio, differences in this ratio are used to compute the arterial oxygen saturation, a value derived empirically, generally through a calibration curve.

Accurate measurement of arterial oxygen saturation, therefore, is highly dependent upon an accurate reading of a pulse waveform. The pulse waveform is typically detected by a sensor disposed on an extremity or, in the case of adults, on the nose or ear. These sensors, however, often do not provide an accurate reading due to the motion artifacts caused by muscle movement, vasoconstriction associated with hypotension, shivering, motion of the body site where a sensor is affixed, or other types of internal or external movement during the measurement process. Other sources of noise are also problematic, in particular electromagnetic, measurement, and intrinsic error sources can also cause noise problems. These noise factors can cause the properties of light or energy attenuation to vary erratically. Traditional signal filtering techniques are frequently totally ineffective and grossly deficient in removing these motion-induced effects from a signal. The erratic or unpredictable nature of motion induced signal components is the major obstacle in removing or deriving them. Thus, presently available physiological monitors generally become inoperative or inaccurate during time periods when the measurement site is perturbed.

Furthermore, the problems associated with detecting proper heart pulses and evaluating blood oxygenation levels are significantly more difficult with respect to fetal monitoring. The fetal oximeter sensing function takes place in a physically constrained environment (the uterus), subject to fetal motion, substantial pressure variations (contractions), and interference by the presence of a variety of fluids in the environment (amniotic fluid, meconium, maternal blood). The sensing must be done using reflectance, rather than transmissive, pulse oximetry, further compromising the signal to noise ratio of the measurement. Despite many attempts at sensor design to improve signal quality, the problem of successfully monitoring in the presence of these many factors has not been solved in the prior art. Furthermore fetal physiology, is characterized by typically low arterial oxygen saturation (often below 50%), and a much lower difference between arterial and venous saturation. For this reason, it is doubtful that some of the advanced algorithms for noise rejection, designed with the assumption of more mature physiology, will function.

Lastly, these inventions tend to either not treat the question of pulse rate extraction from the plethysmographic waveform, or present solutions not ideal for the fetal physiology and environment. Fetal heart rate (FHR) measurement is currently the most important parameter monitored in utero to detect signs of fetal distress. Typically, FHR is determined by intermittent manual auscultation through the mother's abdomen by a trained caregiver, or by means of an ECG electrode screwed into the fetal scalp. Thus a means of reliable non-invasive pulse rate determination in fetal monitoring would offer a significant improvement over the prior art.

For example, one method for dealing with noise problems is described in U.S. Pat. No. 5,588,425 to Sackner et al. Here, a narrow range of systolic upstroke times are empirically defined and waveforms are deemed valid only if they fall within the predetermined range. The system, therefore, depends on a consistent, narrow range of upstroke times for all patients to be effective. These values may not apply adequately to fetal monitoring situations. Furthermore, irregular pulses which may provide valuable diagnostic information, are ignored.

Another method for removing noise from a pulse waveform signal is disclosed in U.S. Pat. No. 5,934,277 to Mortz. Mortz discloses a system wherein statistical techniques such as linear regression and correlation are used to filter noise from the signal. This system requires a significant amount of pre-calculation filtering to assure that the input signals from both the red and infrared are consistent. Furthermore, "good data" must be identified before a calculation can be made. For example, if the processed signal contains a significant variation in evaluated points, the system will determine that "good data" has not been achieved. If the data is insufficiently "good" an alarm is set for the user. This system, therefore, is only capable of processing data in a well-defined "good" range, and cannot filter noise factors sufficiently to provide a useable signal in many applications, particularly in fetal applications.

U.S. Pat. No. 5,687,722 to Tien et al. also discloses a system based on a regression algorithm. Here, incoming data is filtered into a number of data windows. A ratio value indicative of oxygen saturation in the patient is statistically analyzed to determine the best estimate for the correct ratio value. Although this algorithm may be capable of extracting oxygen saturation information from non-optimal signals, it does not yield a pulse rate value. In fetal monitoring, where alternative sources of continuous pulse rate information are inconvenient, these situations algorithms of this type are insufficient.

Although the problem has been described mainly with reference to pulse oximetry systems, a similar problem exists in conjunction with a number of different types of physiological monitoring including electrocardiographs, blood pressure, capnographs, heart rate, respiration rate, and depth of anesthesia, for example. Other types of measurements include those which measure the pressure and quantity of a substance within the body such as breathalyzer testing, drug testing, cholesterol testing, glucose testing, arterial carbon dioxide testing, protein testing, and carbon monoxide testing, for example. In all of these types of monitoring, the ability to derive an accurate pulse waveform is extremely important in providing an accurate physiological reading.

SUMMARY OF THE INVENTION

The present invention relates generally to a method of signal processing for use with physiological monitoring or other types of monitoring which involve signals containing a relatively low dominant frequency (order of Hz to tens of Hz), with intermittent broad-band noise of significant amplitude. The signal processing method of the present invention can be used to locate the fundamental period in a noisy input signal, filter noise from the signal, and reconstruct the signal in a real-time processing environment without the necessity for filtering "good" data samples or limiting the range of expected good data points. Furthermore, the method of the present invention can distinguish small signals from random noise in the same frequency range.

A numerical transform analogous to a Fourier transform is applied to input data to provide a data set that contains signal amplitude versus period of the input waveform. The independent variable in the numerical transform is a period, as opposed to the frequency value generally employed in a Fourier transform. For example, a discrete Fourier transform is defined as:

$$X(k) = \Sigma^{N-1}_{n=0} x(n) e^{-j2\pi kn} k = 0 \ldots N-1$$

such that the independent variable is frequency which is varied as integer multiples of the fundamental frequency (1f, 2f, 3f, ... Nf). The present invention instead employs an algorithm wherein the transform is performed at incremental steps of the period, $\Delta T$. A transform, comprising a summation of data points multiplied by samples of a sine wave and cosine wave of a period equivalent to $\Delta T$, is calculated for each period $\Delta T$ between a pre-selected minimum and maximum period. This transform generates spectral data for a limited set of periods, but at the resolution of the sampling rate. The transform can be used to find periodic functions buried in noise from real-time processes, and is particularly useful in physiological monitoring such as blood pressure monitoring, pulse oximeters, and fetal pulse oximeters. Furthermore by establishing an ensemble average from the calculated transform, the noise associated with the process can be filtered and the input signal can be reconstructed.

The method of the present invention can be advantageously used for digital signal processing of an analog input signal. The digital signal processing method generally comprises the steps of sampling an analog input signal at a sampling rate of $\Delta T$, multiplying each of the sampled data points times a pair of orthogonal basis functions, preferably a sine and a cosine wave, and providing a summation of these points over the established period, in accordance with the equation listed above. The resultant data can then be evaluated to locate the peak power in the waveform, or processed as an ensemble average to reconstruct the input signal while filtering extraneous noise. It will be apparent to one of ordinary skill in the art that an alternative pair of orthogonal basis functions may be determined and used. This choice may be made to enhance extraction of particular signals with an inherently non-sinusoidal character.

To provide a signal processing algorithm with sufficient speed to provide a transform of a real time input signal, a number of steps can be taken to increase the efficiency of the algorithm. For example, a more time-efficient algorithm similar to a sliding Fast Fourier Transform can be used to increase the speed of the calculations. Furthermore, a single buffer of sine data, and correspondingly a single buffer of cosine data, can be mathematically manipulated to provide a number of sine and cosine waves of various periods without the need for recalculating the value at each step in the period, as will be described more fully below.

Other advantages and features of the invention, together with the organization and manner of operation thereof, will become apparent from the following detailed description when taken in conjunction with the accompanying drawings

DETAILED DESCRIPTION OF THE PREFERRED EMBODIMENTS

Figures 1, 2, 3, 4:
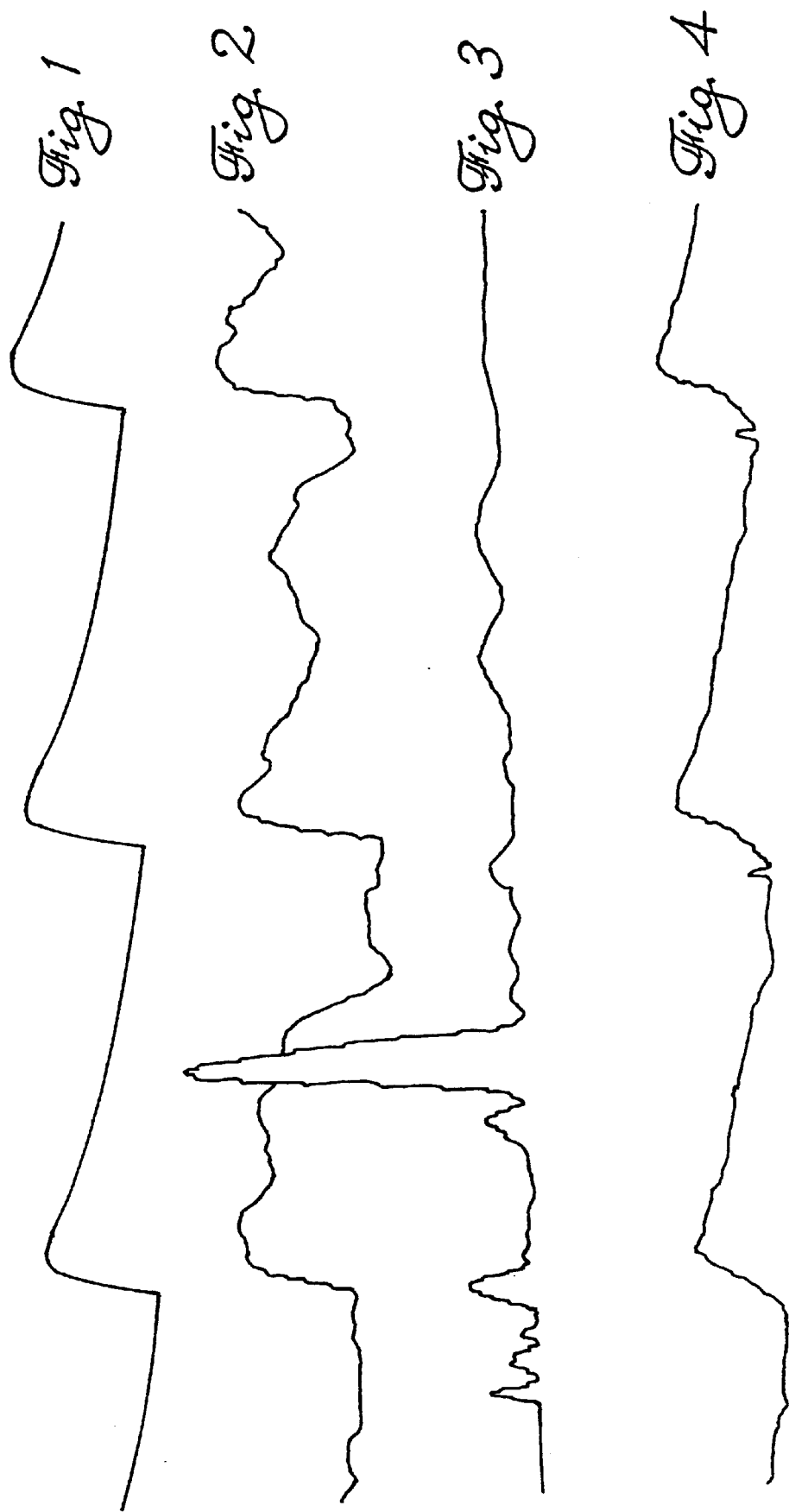
FIG. 1 is a waveform of a typical periodic physiological signal.
FIG. 2 is a waveform of a typical periodic physiological signal with noise aded.
FIG. 3 is a transform of the waveform of FIG. 2 produced in accordance with the present invention.
FIG. 4 is a waveform reconstructed from the transform of FIG. 3.

Referring now to the Figures and more particularly to FIGS. 1–4, a number of signals important in describing the present invention are shown. FIG. 1 is a representation of a physiological signal without a noise component. As noted above, physiological signals are generally periodic signals with a period of less than three seconds. FIG. 2 is a representation of the signal of FIG. 1 with an added noise component. This signal represents an average input signal from a real-time physiological process, where noise from motion artifacts and other extraneous sources substantially buries the periodic input signal of FIG. 1. FIG. 3 is a representation of a transform of the signal, where the transform is a representation of amplitude versus period, and is calculated with a method in accordance with the present invention. Finally, FIG. 4 is a representation of a signal produced through an ensemble averaging procedure to provide a reconstruction of the signal of FIG. 1.

The input signal of FIG. 2 can be processed in a number of different ways depending on the application. In all of these cases, the analysis is analogous to a known type of Fourier transform, wherein, instead of varying the signal over integer multiples of a fundamental frequency, the abscissa of the output transform comprises multiples of sample points, $\Delta T$. For example, if it is not necessary to provide a real time analysis of the input signal, processing techniques analogous to the Digital Fourier Transform and the Fast Fourier Transform can be employed to calculate the numerical transform.

The present invention, however, can be employed for determining the period of and filtering noise from a physiological input signal in real time. To provide a real-time analysis of the input signal, an analysis method analogous to a Sliding Fast Fourier Transform (SFFT) can be used. The Sliding Fast Fourier Transform is discussed in "Sliding FFT Computes Frequency Spectra in Real Time", EDN, Sep. 1988, page 161. This article is hereby incorporated by reference. As discussed in this article, the SFFT differs from an FFT in that the SFFT "slides" over a data sequence N points at a time. The SFFT, is based on fact that the FFT of the n+1th sampling interval is equal to the phase shifted sum of the previous FFT and the difference between the newest sample and the oldest, or between the sample entering a buffer of data at interest and the sample leaving the same buffer of data. The FFT, on the contrary, first accumulates N points, then performs a transform, accumulates a second set of N points, then performs a transform, etc. The SFFT therefore, requires significantly less computing time than the standard FFT algorithm and can be used to provide a real time signal analysis.

Applying this theory to the problem of processing a physiological signal in real time, the analog input signal of FIG. 2 must initially be sampled. Physiological signals, and particularly physiological signals related to blood pressure or oximetery, are generally sampled at a rate of one hundred to two hundred samples per second. This sampling rate provides a sufficient sample of the input signal without aliasing. For purposes of simplifying the following discussion, we will assume a sampling rate of one hundred samples per second, or ten milliseconds per sample. It will be apparent to one of ordinary skill in the art, however, that other sampling rates could be used, and furthermore that the selected sampling rate can be varied based for uses outside of the field of physiological monitoring.

Generally, samples are collected for a period of time substantially equivalent to the maximum expected period of the noise-free physiological signal (FIG. 1). Physiological signals representing cardiac activity, for example, are expected to have a predominant period (the cardiac period) of less than three seconds. Therefore, samples are collected for a period of at least about three seconds. For the assumed sampling rate of ten milliseconds, at least three hundred samples will be collected for transform evaluation to commence. The input data will generally be stored in an array or buffer. Although specific period and sampling values have been described, it will be apparent to one of ordinary skill in the art that a buffer of any size greater than the maximum expected period divided by the sampling rate could also be used. Furthermore, in some applications wherein the data is evaluated for signals of a given period, a smaller buffer can also be used. In applications in which data is analyzed after collection is completed and is not being evaluated in real time, this data can be stored in a fixed array. When the data is continuously collected, a type of buffer known as a ring buffer may be employed, in which new data overwrites old, previously processed data. Other means of storing data continuously for a limited know will be apparent to one of ordinary skill.

For purposes of calculating the transform of the input signal shown in FIG. 2, buffers are also established for two orthogonal waves, preferably a cosine and a sine wave. The sine and cosine, or other orthogonal waves, are each defined to have a period equal to that of the maximum expected period, as discussed above. In the present example, therefore, the cosine and sine buffers each contain a waveform having a length of three seconds. The sine and cosine buffers herein each contain three hundred data points, where these data points represent the sine and cosine wave at ten millisecond intervals. These mathematical functions vary in the range of −1.0 and +1.0, but to permit the use of fixed-point or integer arithmetic in a microprocessor, the cosine and sine wave stored value points are preferably multiplied by a scaling factor to maintain significant digits in the calculation. This avoids the need for use of floating-point calculations. For example, when a sixteen bit processor is used in a real-time embedded system, the sine and cosine values may be multiplied by 4096 ($2^{12}$). Scaling by a power of two permits rapid rescaling of the results of calculations utilizing binary shift operations, rather than multiply and divide operations. Note that, although buffers of stored cosine and sine values have been established for this calculation, in some applications the cosine and sine values can be calculated as required, and in other applications these values may be pre-calculated and stored as a table of predetermined values in non-volatile memory.

Figure 5:
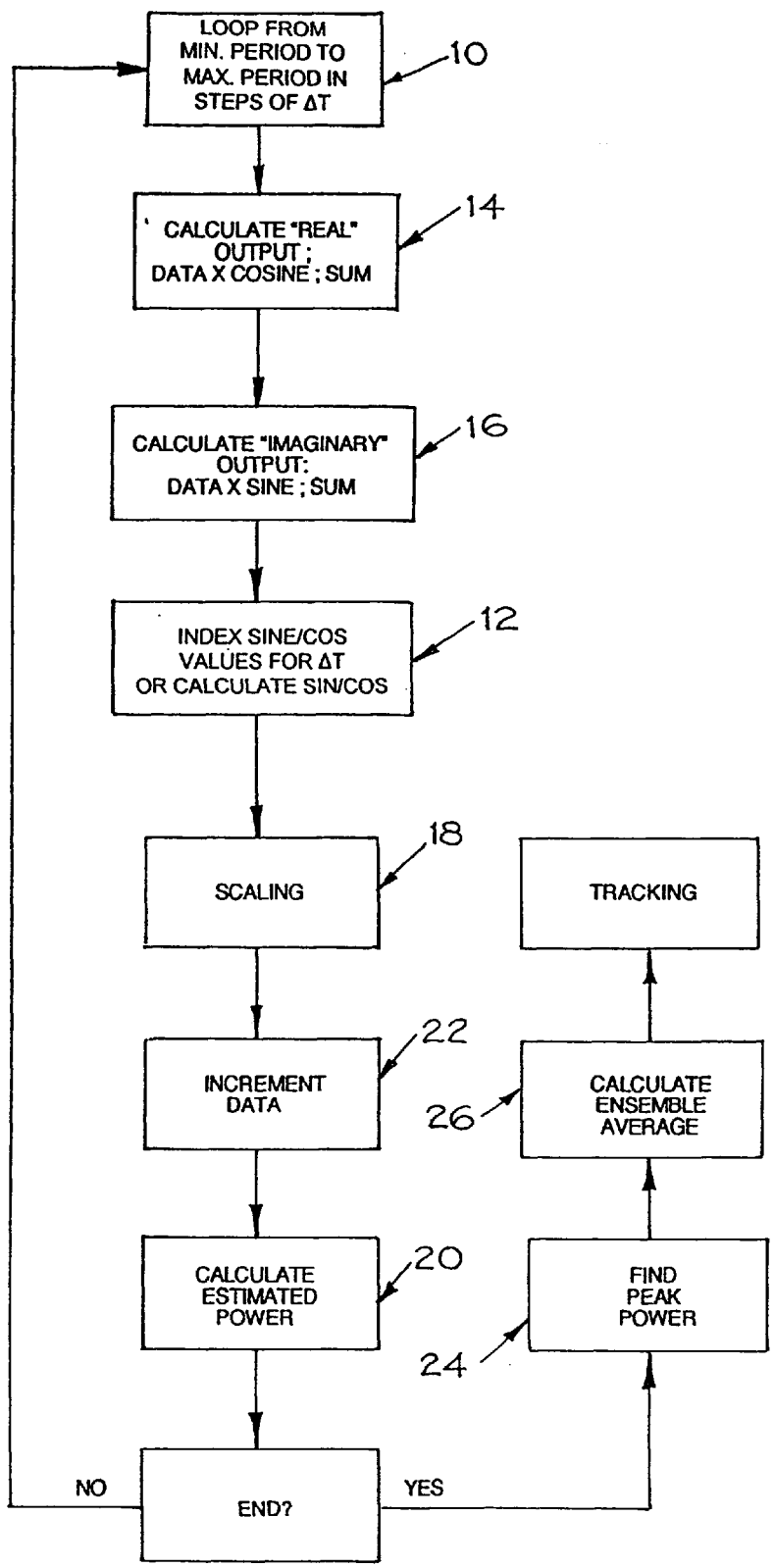
FIG. 5 is a simplified flow chart of a transform performed in accordance with the present invention.

Referring now to the C language code segments below, and the corresponding flow chart of FIG. 5, wherein the numerals correspond to the line numbers in the code, one method for performing the numerical transform of the present invention is shown. In the code below, the sine and cosine waves are stored in the variables ei and er, respectively, and the output of the transform is contained in the variables yr and yi. Two pointers xp and wp point to data in the input buffer, where xp points to the beginning of the buffer, or to new data, and wp is a working pointer which points to some location in the buffer, and can point to the oldest data in the buffer. The variable dr contains input data, and is initially initialized to the difference between the newest and oldest data. The variable j is a loop counter which provides a loop from the maximum selected period (MAX_PERIOD, or three seconds in this example, as described above), to the minimum selected period (MIN_PERIOD, or two hundred milliseconds for this example), at steps of ten milliseconds. An additional variable k is used to index the cosine and sine wave buffers er and ei respectively. The variable k is incremented based on the values held in cntr[j] and inx[j] as will be described below.

```
for(i=0; i<MAX_PERIOD; i++)
{
    cntr [i] = 0;                                    Line 2
    yr[i] = yi[i] = 0;
    inx[i] = 19660800 / (i+1);                       Line 4
    er[i] = 4095 * cos((TWO_PI * i) / N);             Line 6
    ei[i] = 4095 * sin((TWO_PI * i) / N);
}
if(++xp > end)
    xp = begin;        /* increment the sample buffer pointer */
dr = new − *xp; /* initial difference of newest and oldest values */
*xp = new; /* save newest value in sample buffer */
wp = xp; /* initial working pointer value */
                                                     for(j=
                                                      MAX_
                                                   PERIOD−1;
                                                 j>=MIN_PERIOD;
                                                     j−−) Line
                                                          10
                                                          {
    k = cntr[j] >> 16;                                Line 8
    yr[j] += dr * er[k];                              Line 14
```

-continued

```
     yi[j] += dr * ei[k];                                    Line 16
     if((cntr[j] += inx[j]) >= 19660800 – j) cntr[j] = 0;    Line 12
     if((wp += RATIO) > end) wp –= NN;                       Line 18
     dr = *xp – *wp;
     yrx = (yr[j]/j) >> 10;                                  Line 20
     yix = (yi[j]/j) >> 10;
     pwr[j] = yrx * yrx + yix * yix;                         Line 22
}
for(l=20, pmax=0; l<N; l++) Line 24
     if( pwr[l]>pmax )
     {
          pmax = pwr[l];
          t0 =l;
     }
     if(t0)tx = (tx + 1)% t0;
     pavg[tx] = pavg[tx] + ((*xp – pavg[tx]) / 8); Line 26
```

Referring again to the code segments above, initialization of data is performed in lines 2, 4, and 6. As noted above, the variable cntr[j] holds values for incrementing k, the index to the sine and cosine waves, initialized in step 6. This array is initially set to zero in line 2. In line 4, the variable inx[j] is initialized. This variable basically holds "step" increments of the sine and cosine waves. As can be seen from line 4, the "steps" are inversely related to the period such that, for small periods, the steps are large, and for large periods, the steps are small. The numerator is essentially equivalent to the maximum period times two raised to the sixteenth power, while the denominator represents the range of periods to be analyzed. The factor in the numerator is for scaling purposes, facilitating the use of integer arithmetic, and can vary depending on the computational hardware system used.

Referring now to line 10, the transform generally comprises a loop from the maximum period to a minimum period in steps j which are preferably equal to the sampling period of ten milliseconds. Line 8 is essentially a scaling function for obtaining the index k from the sine and cosine wave counter value cntr[j]. As noted above, the value of cntr[j] is initially set to zero such that, for the first loop, the cosine and sine values ei and er are evaluated as the cosine of zero and the sine of zero. The data value dr is multiplied times the cosine value and stored in the output variable yr[j], and multiplied times the sine value and stored in the output variable yi[j]. As the loop is successively processed, the variables yr[j] and yi[j] are continually added to the previous values to provide a summation of these calculated values.

Figure 6:
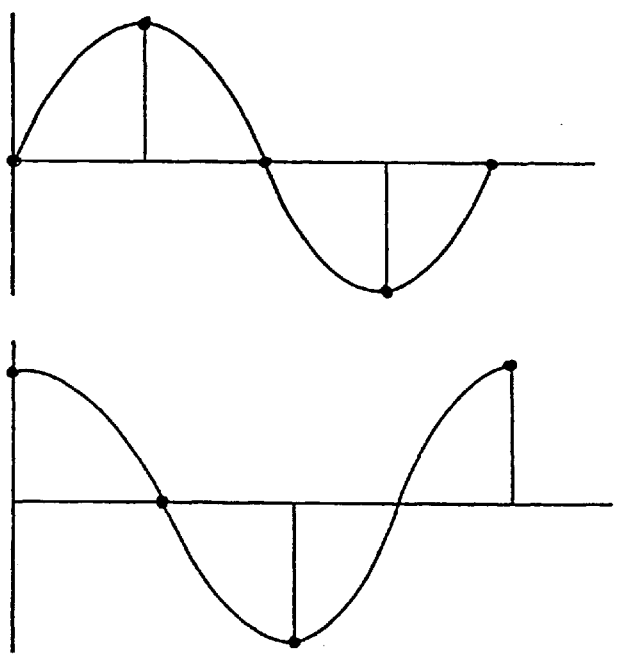
FIG. 6 is a representation of the sine and cosine wave points used in the present method when the period is small.
Figure 7:
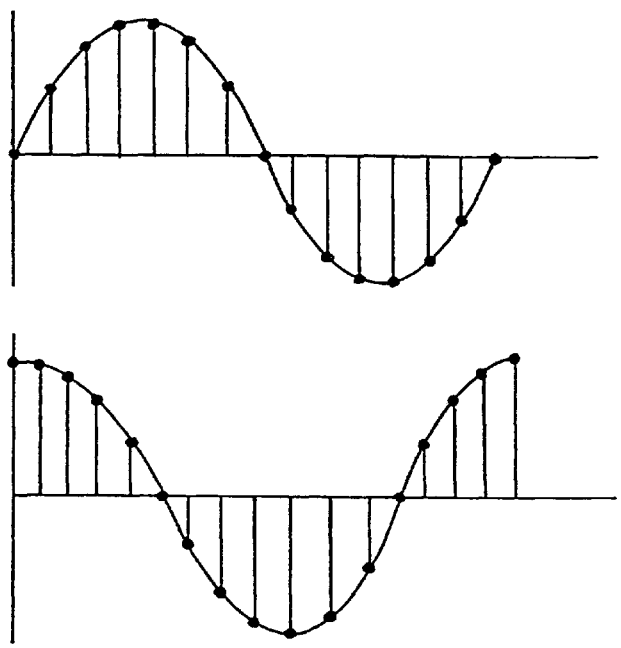
FIG. 7 is a representation of the sine and cosine wave points used in the present method when the period is large.

In line 12, the counter value to the index k of the sine and cosine waves is incremented by the value inx[j]. Since inx[j] is a constant for each value of j, the changing value in cntr[j] will increase incrementally as inx[j], 2*inx[j], 3*inj[j], etc. as the loop is successively processed. Therefore, the calculations of yr[j] and yi[j] are made at equally spaced increments of the sine wave which vary depending on the value j. As noted above, however, the value inx[j] is large when the period (j) is small. Therefore, for small periods, the number of steps taken through the sine and cosine waves is small, and a number of points in each wave are skipped. For example, for an extremely low period, the transform may be performed only at the cross-over points of the waveform and at the peak, as shown in FIG. 6, while for a large period approaching the maximum selected period, the sine and cosine waves will be evaluated at each ΔT (j) defined, as is seen in FIG. 7. The effect of this procedure is to provide a number of sine waveforms and cosine waveforms of varying periods by decimation of the maximum-length period in the stored buffer of data. Although the sine and cosine data is shown stored in an array which is indexed to provide an appropriate waveform for the period, in alternate applications, appropriate cosine and sine wave values can be determined when necessary. In this case, the period of the cosine and sine waves can be changed to match the period of the step ΔT (j).

The resultant output values yr and yi are scaled in line 12 so that the results for all periods will be given an equal weight. In line 18, the data buffer is incremented and the oldest data in the buffer is subtracted to provide the "slide" of data as described above The results yr and yi are used to calculate an array of estimated power values for each period in line 20. Note that this estimated power involves adding the square of the real part and the square of the imaginary part of the signal. Although this is sufficient for purposes of comparison of signal power at different periods, if desired a numerically exact value can be obtained by taking the square root of the resultant value. Note that although a specific scaling function has been shown, it will be apparent to one of ordinary skill in the art that the scaling factors used are dependent on the selected values and that these factors may be different or may be unnecessary depending on the computing system used.

Upon completion of the loop, the arrays of power values are preferably evaluated for a "peak" power (line 24). The peak power factor indicates the dominant period of the actual input waveform. The resulting graph of signal power versus period is shown in FIG. 3. As shown here, the recalculation of signal power at each period in lines 20–22 is being performed for every incoming sample. However, in some applications it is sufficient to recalculate the power from time to time. This can reduce the computational overhead of the transform significantly. In this case, the calculation of yrx, yix and thus pwr[j] can be deferred to the peak power determination at line 24.

As shown, the peak power is determined by a simple comparison. It will be apparent to those of ordinary skill in the art that other methods for finding the peak value can also be used. Furthermore, in some applications, filtering to remove "jitter" or other noise can be employed to "smooth" the resultant output. For example:

```
local power(i) = (pwr[i–1] + 2*pwr[i] + pwr[i+1])/4;
for (l = MIN_PERIOD+1, pmax = 0; l<MAX_PERIOD; l++)
{
    p = local_power(l);
    if (p > pmax)
    {
        pmax = p;      /* pmax = highest smoothed power */
        t0 = l+1;      /* t0 = period at highest power */
    }
}
```

Another enhancement is to apply a local curve fit in the vicinity of the peak identified by the basic algorithm. Using a small number of points in the period data surrounding the initial peak, this can improve the period estimate to better than the resolution based on the sampling period, as well as improve the estimate of the power at that peak. A quadratic curve fit can be implemented easily for this purpose, although other functional forms are possible.

Other statistics useful for period domain analysis are easily extracted:

```
for (1 = MIN_PERIOD, psum = 0; 1<=MAX_PERIOD; 1++)
    psum += pwr[1];
average_power = psum / (MAX_PERIOD-MIN_PERIOD+1);
and:
for (1 = MIN_PERIOD, psum = 0; 1<=MAX_PERIOD; 1++)
    if (pwr[1] > average_power/2)
        psum++;
percent_high = 100*psum / (MAX_PERIOD-MIN_PERIOD+1);
```

The average_power statistic gives a way to compare power results through time despite overall signal power changes. The percent high gives a measure of the concentration of power in the signal, i.e., whether total power is concentrated in a few peaks or many peaks.

One use of the power statistics derived from the above transform is to facilitate extraction of a signal of a particular period from a combination of signal and noise. To reconstruct the waveform, if necessary, an ensemble average can be calculated as shown in step 26.

Here pavg[ ] is an array representing a continuously updated ensemble average of a signal repeating with a dominant period found to be t0 using the above transform. The current index in the ensemble, tx, is incremented, then reduced modulo t0. After this operation, the new index will be less than the length of the dominant period, in samples. This has the effect of realigning the incoming data to match the period of data already in the buffer, effectively slicing up the incoming waveform into t0-sized pieces and stacking them up. The latest sample, *xp (the value at the location xp in the input signal buffer), is factored into the appropriate point of the ensemble with an averaging operation. A running average calculation (the digital equivalent of an IIR filter) is shown, but alternative averaging schemes such as a moving average may also be employed. In the running average, for each point of the ensemble the current value is incrementally reduced when the new value is summed in. The effect is to merge the stack of waveform slices, most heavily weighting the most recent slices. The resultant reconstructed waveform is shown in FIG. 4.

Frequently, extraction of period information alone is sufficient, without waveform reconstruction. In alternate embodiments one or more peaks in the period data, e.g., cardiac period, are tracked to enhance signal processing in the presence of significant corrupting noise in the same period range of interest as the signal data. As previously noted, physiological signals typically demonstrate nonstationary statistics; but in the absence of serious arrhythmias, the cardiac period can be tracked dynamically. This is generally a valid assumption in fetal monitoring.

A typical implementation for period tracking would look something like this:

```
#define INITIALIZING   0
#define SEARCHING      1
#define TRACKING       2
int update (void)   /* returns currently tracked period or 0 if none */
{
    static int tracking_state=INITIALIZING, track=0, lost=0;
    int peak;
    /* gets average_power and percent_high */
    power_statistics (MIN_PERIOD, MAX_PERIOD,
        &average_power, &percent_high);
    switch (tracking_state)
    {
    case TRACKING:
        if (percent_high>MAX_HIGH)
            lost++;         /* power too diffuse, probably noise */
        else
        {   /* search around current track for peak */
            peak = peak_power (track-DELTA,track+DELTA);
            if (local_power(peak) < 2*average_power)
                lost++;     /* no strong peak here any more */
            else
            {   /* peak still present, keep tracking */
                track = peak;
                if (lost)
                    lost--;
            }
        }
        if (lost < MAX_LOST)
            break;          /* track still viable, use result */
    default:                /* start or restart search for peak*/
    case INITIALIZING:
        track = 0;
        lost = 0;           /* fall through to restart search */
        tracking_state = SEARCHING;
    case SEARCHING:
        peak = peak_power(MIN_PERIOD, MAX_PERIOD);
        if (qualified(peak)) /* test candidate with other criteria */
        {
            track = peak; /* acceptable, track it */
            tracking_state = TRACKING;
        }
        break;
    }
    return (track);
}
```

Here the update( ) function is assumed to be called once per second, although the frequency may be modified as appropriate. The "track" value is the period of interest, followed through time as it varies. Note that a certain amount of hysteresis is built into the algorithm (as specified by the MAX_LOST parameter) so that short periods of unacceptable signal can be ignored.

Several enhancements of the basic tracking algorithm will be apparent to those of ordinary skill in the art. The qualified( ) function may integrate other sources of information to improve the accuracy of peak selection. This information may include for example time domain analysis of the signal, a priori knowledge of the signal source based on physiology or clinical status, etc. Additionally, such information can be used to find other possible tracking candidates, directing the period domain search if the global peak is not qualified for use (e.g., because it is found to correspond to noise).

The "track" result may be further averaged to reduce jitter and improve the resolution of the period estimate beyond the limitation of sampling period. Finally, a rate calculation is simply the inverse of the period. A simple moving average algorithm combined with rate calculation (per minute) can be implemented as follows:

```
int calculate_rate (int period)
{
    static int ring[LENGTH], index, valid; /* static variables */
    int I, rate;
    if(period < 0)
    {   /* initialization */
        for (I=0; I<LENGTH; I++)
            ring[I] = 0;
        rate = 0;
        index = 0;
        valid = 0;
```

-continued

```
    sum = 0;
}
else
{   /* update with latest period */
    if (ring[index]!= 0)
    {   /* remove oldest value from sum */
        valid--;
        ring_sum -= ring[index];
    }
    if (period != 0)
    {   /* add in new period, if valid */
        valid++;
        sum += period;
    }
    ring[index] = period;
    if(++index == LENGTH)
        index = 0; /* wrap around ring index */
    if (valid) /* if sufficient data, calculate rate */
        rate = (60 * SAMPLES_PER_SEC * valid + sum/2) / sum;
    else
        rate = 0; /* no current rate estimate */
}
return (rate);
}
```

Here the calculate_rate( ) function is assumed to be called once per second, although the frequency may be modified as appropriate. The ring LENGTH is chosen for an appropriately smoothed rate result with sufficient responsiveness to change.

Generally, therefore, the transform of the present invention can be used to digitally process a low frequency, high noise analog input signal. The input signal is preferably initially sampled to provide a real-time digital input signal. The sampled data points are preferably stored in a buffer and evaluated through a numerical transform. Each of the data points can be multiplied, point by point, by a sampled pair of periodic orthogonal waveforms, and the results summed to provide a summation for each data point. Furthermore, the orthogonal waves are preferably indexed to provide waves of a smaller period when the examined period is small, and of a large period when the examined period is large. The relative strength of contribution of each possible period is calculated as the power of each period. To increase the speed of the calculations for real-time applications an algorithm analogous to a sliding Fast Fourier Transform is used. After determination of the power at each possible period, this information may be used in signal reconstruction or to locate and track periods of interest.

Figure 8:
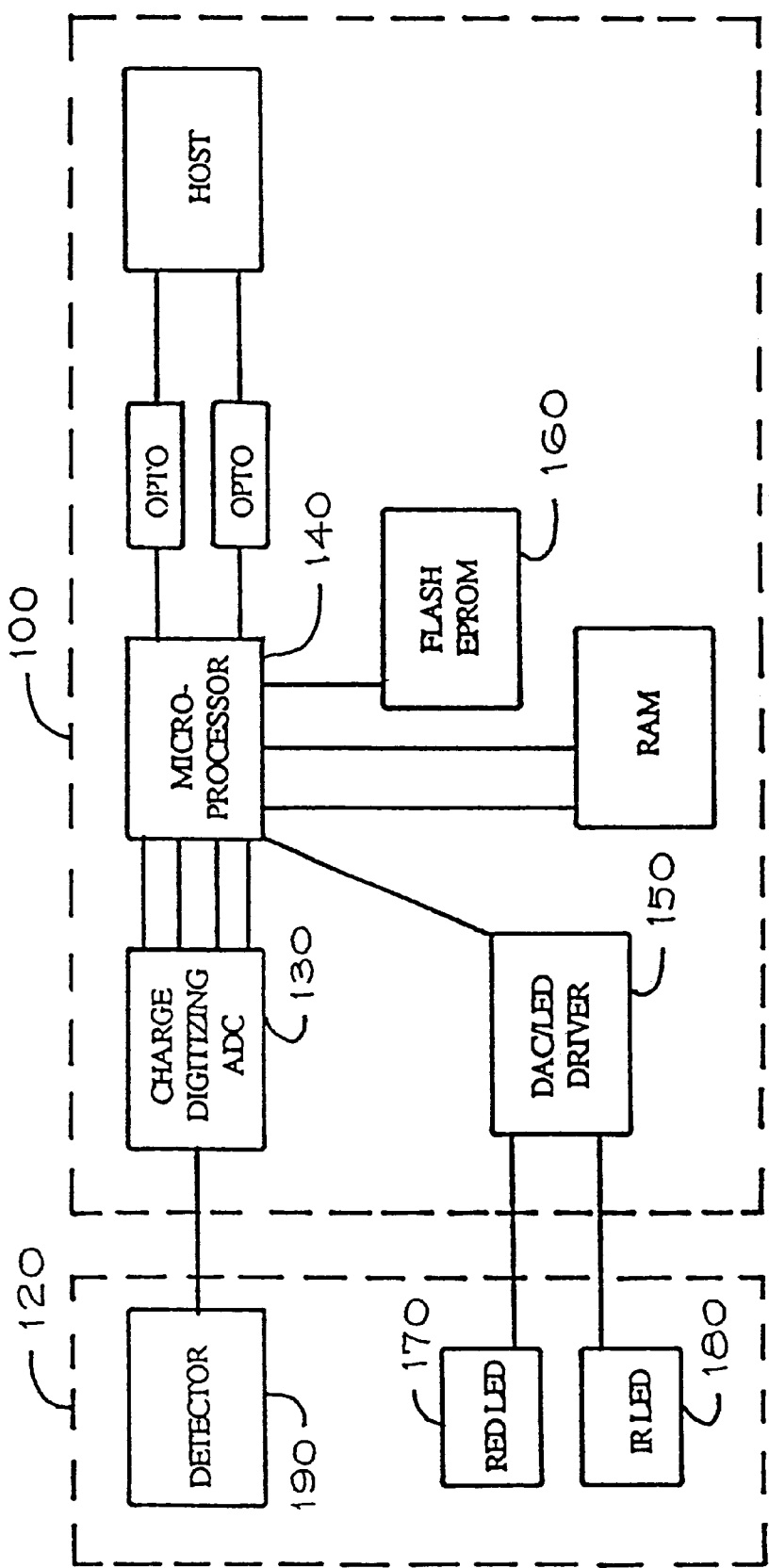
FIG. 8 is a block diagram of an oximeter constructed in accordance with the present invention.

As noted above, the present invention can be used advantageously in pulse oximetry, and provides a substantial advantage over prior art systems when used with fetal monitoring systems, and especially for fetal oximetery. Referring now to FIG. 8, a block diagram of a pulse oximeter system 100 is shown. The pulse oximeter system 100 used in conjunction with the present invention can be a digital oximetery system as described in U.S. Pat. No. 5,842,981, which is hereby incorporated by reference. The digital oximeter provides an advantage because analog signal processing steps which can induce additional noise in the system are substantially eliminated. However, although a digital oximeter system is described, other known types of oximeters can also be employed with the method of the present system to increase the integrity of the monitored signals. The sensor 120 can be any of a number of types of known sensors. These devices are generally coupled to a digit or an extremity of an adult body. For fetal monitoring, an inter-uterine sensor device such as that described in U.S. Pat. No. 5,425,362, which is also incorporated herein by reference, is preferably used. However, other types of fetal sensor devices can also be used. As noted above, in fetal monitoring, sensing must be done using reflectance, rather than transmissive, pulse oximetry. This approach involves transmitting a light source of at least one and preferably more than one wavelength to illuminate blood containing tissue of the fetus. The reflected light is then detected and evaluated for purposes of determining the blood oxygenation saturation. Although the light sources can be a red LED 170 and infrared LED 180 as shown, it will be apparent to one of ordinary skill in the art that other types of light sources such as laser diodes can also be used. Furthermore, variations in the wavelength of the light used can also be made.

Referring again to FIG. 8, the reflected light is preferably detected by a photodetector 180. The output of the photodetector is digitized and transmitted to the microprocessor 140, which samples the input signal for processing in accordance with a method of the present invention. Alternatively, a fiber optic line may carry the light itself to and/or from the sensor to the microprocessor, where a photodetector and digitizer would be located.

In operation, the pulse oximeter system 100 generally determines a blood oxygen saturation level in accordance with known methods based on an input plethsymographic wave received at an input port which is preferably coupled to the analog to digital converter 130. As noted above, oximeters determine the difference between background absorption (essentially a dc value) during diastole and peak absorption (essentially a pulsatile ac component) during systole at both red and infrared wavelengths. This difference corresponds to the absorption caused by arterialized blood. Since the red:infrared light absorption ratio is indicative of oxygen saturation, differences in this ratio are used to compute the arterial oxygen saturation. This ratio is calculated in the microprocessor 140. The oxygen saturation value is determined empirically, generally by comparison of the red:infrared ratio to tabular data stored in memory 160. The heart pulse rate is generally determined by counting the pulsatile components. However, in some cases, and especially in fetal monitoring, these pulsatile components are insufficiently strong and both oxygenation calculations and heart rate information can be lost. The method of the present invention can be implemented through the micrprocessor 140 to calculate the dominant period in the waveform, and hence the cardiac period, to better determine the heart rate. The method of the present invention can also be used to provide a track of the pulse rate, as defined above.

In one embodiment of the invention, the pulse rate is preferably calculated by counting the number of pulsatile components, as described above. The microprocessor 140 can monitor the resultant values to determine whether the heart rate is inconsistent, for example, if the number of pulsatile components is not sufficiently large. This is a problem which is particularly prevalent in fetal monitoring, where the pulsatile component is often not significantly greater than the background component and is therefore difficult to detect. When this condition occurs, the microprocessor 140 can process the input signals with the transform described previously to locate the pulse rate or heart beat. The input data, therefore, can be processed in accordance with the method described over only as necessary. In alternative embodiments, however, the method of the present invention can be used to maintain an accurate account of the heart rate in all situation.

While preferred embodiments have been illustrated and described, it should be understood that changes and modifications can be made thereto without departing from the invention in its broadest aspects. Various features of the invention are defined in the following claims.

We claim:

1. A method of signal processing for filtering noise from an input signal, wherein the input signal is noisy, the method comprising the following steps:
   (a) calculating a numerical transform of the input signal to determine a fundamental period, wherein the numerical transform is calculated at each of a plurality of incremental periods by multiplying samples of the input signal by first and second periodic orthogonal waveforms of period equal to the selected incremental period;
   (b) indexing through a buffer storing the first periodic waveform and a buffer storing the second periodic waveform, where the index is inversely proportional to a selected period to selectively decimate the length of the period;
   (c) scaling and summing the calculated numerical transforms for a given incremental period to yield the fundamental period in the input signal; and
   (d) utilizing the fundamental period for filtering noise from the input signal.

2. The method as defined in claim 1, further comprising the step of calculating an ensemble average to reconstruct the input signal.

3. The method as defined in claim 1, further comprising the step of calculating the power spectrum for each transform creating a power versus period buffer.

4. The method as defined in claim 3, further comprising the step of tracking a period of interest in the input signal through time by locating and tracking its peak in the power versus period buffer.

5. The method as defined in claim 1, wherein the input signal is a plethysmographic wave.

6. The method as defined in claim 1, wherein the input signal is a plethysmographic signal from a pulse oximetery sensor.

7. The method as defined in claim 1, wherein the input signal is a plethysmographic signal from a fetal pulse oximeter.

8. The method as defined in claim 1, wherein the input signal is slid through the transform such that a new data point is added and an old data point is subtracted for each iteration.

9. New The method as defined in claim 1, wherein the input signal is a physiological signal.

10. The method as defined in claim 1, wherein the input signal contains a dominant frequency of up to tens of hertz with intermittent broad band noise, wherein the frequency range of the broad band noise has a broad band noise period range in the same period range as the fundamental period.

* * * * *

UNITED STATES PATENT AND TRADEMARK OFFICE
CERTIFICATE OF CORRECTION

PATENT NO.    : 6,647,280 B2
DATED         : November 11, 2003
INVENTOR(S)   : Dennis E. Bahr and James L. Reuss It is certified that error appears in the above-identified patent and that said Letters Patent is hereby corrected as shown below:

<u>Title page,</u>
Item [74], *Attorney, Agent, or Firm*, should read:
-- Reinhart Boerner Van Deuren s.c --

<u>Column 6,</u>
Line 6, "resealing" should read -- rescaling --
Lines 55-64, of the C language code segment should read:

```
{
if(++xp > end)
    xp = begin;        /*increment the sample buffer pointer*/
    dr = new -*xp;     /*initial difference of newest and oldest values*/
    *xp = new;         /*save newest value in sample buffer*/
    wp = xp;           /*initial working pointer value*/ for(j=MAX_PERIOD-1; j>=MIN_PERIOD; j--)      Line 10
    {
```

<u>Column 14,</u>
Line 20, the word "New" should be deleted.

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,647,280 B2
DATED : November 11, 2003
INVENTOR(S) : Dennis E. Bahr and James L. Reuss It is certified that error appears in the above-identified patent and that said Letters Patent is hereby corrected as shown below:

Title page,
Item [74], *Attorney, Agent, or Firm*, should read:
-- Reinhart Boerner Van Deuren s.c --

Column 6,
Line 16, "resealing" should read -- rescaling --
Lines 55-64, of the C language code segment should read:

```
{
if(++xp > end)
    xp = begin;         /*increment the sample buffer pointer*/
dr = new -*xp;          /*initial difference of newest and oldest values*/
*xp = new;              /*save newest value in sample buffer*/
wp = xp;                /*initial working pointer value*/ for(j=MAX_PERIOD-1; j>=MIN_PERIOD; j--)     Line 10
{
```

Column 14,
Line 20, the word "New" should be deleted.

This certificate supersedes Certificate of Correction issued April 13, 2004.

Signed and Sealed this

Third Day of May, 2005

JON W. DUDAS
*Director of the United States Patent and Trademark Office*